United States Patent [19]

Michl

[11] Patent Number: 5,213,615
[45] Date of Patent: May 25, 1993

[54] DENTAL MATERIAL AND METHOD FOR THE CONTROL OF CARIES AND PARADENTITIS

[75] Inventor: Rudolf J. Michl, Schaan, Liechtenstein

[73] Assignee: Ivoclar AG, Liechtenstein, Liechtenstein

[21] Appl. No.: 317,578

[22] Filed: Mar. 1, 1989

Related U.S. Application Data

[63] Continuation of Ser. No. 106,215, Oct. 9, 1987, abandoned.

[30] Foreign Application Priority Data

Oct. 11, 1986 [DE] Fed. Rep. of Germany ....... 3634697

[51] Int. Cl.$^5$ ............................................. C09K 3/00
[52] U.S. Cl. .................................. 106/35; 424/435; 424/440; 424/441; 433/199.1; 433/201.1; 433/202.1
[58] Field of Search ................. 106/35; 424/440, 435, 424/441, 49; 433/199.1, 201.1, 202.1

[56] References Cited

U.S. PATENT DOCUMENTS

| | | | |
|---|---|---|---|
| 3,390,456 | 7/1968 | Deleva | 433/217.1 |
| 3,956,480 | 5/1976 | Dichter et al. | 424/54 |
| 4,040,844 | 8/1977 | Grecco | 106/35 |
| 4,041,149 | 8/1977 | Gaffer et al. | 424/57 |
| 4,226,848 | 10/1980 | Nagai et al. | 424/19 |
| 4,466,954 | 8/1984 | Ichikawa et al. | 424/50 |
| 4,476,107 | 10/1984 | Schmolka | 424/49 |
| 4,657,592 | 5/1987 | Takubo | 106/35 |
| 4,695,463 | 9/1987 | Yang et al. | 424/440 |
| 4,713,243 | 12/1987 | Schiraldi et al. | 424/151 |

FOREIGN PATENT DOCUMENTS

| | | | |
|---|---|---|---|
| 0128655 | 12/1984 | European Pat. Off. | 106/35 |
| 0223245 | 5/1987 | European Pat. Off. | 106/35 |

OTHER PUBLICATIONS

European search report.
Thaw "The effects of drug and water incorporation upon . . . " *J. Biomed. Mater. Res.* vol. 15(1) 1981 pp. 29-36.
Luoma "Participation of phosphate of bacterial origin in the . . . " *Caries Res.* vol. 9(3) 1974 pp. 211-223.
Derwent Abs. X-RAM—C84-D76210 of JP59101417 1984 (Lion).

*Primary Examiner*—Paul Lieberman
*Assistant Examiner*—John Boyd
*Attorney, Agent, or Firm*—Cushman, Darby & Cushman

[57] ABSTRACT

A dental material for the control of caries and paradentitis is described, which contains an active agent combination of thymol and/or carvacrol and chlorhexidine and/or the physiologically compatible salts thereof.

The dental material can be a dental varnish or a material such as a dental cement and the like, which remains in the oral cavity for a long period and from which the active combination can diffuse out.

7 Claims, No Drawings

DENTAL MATERIAL AND METHOD FOR THE CONTROL OF CARIES AND PARADENTITIS

This is a continuation of application Ser. No. 106,215, filed Oct. 9, 1987, abandoned.

BACKGROUND OF THE INVENTION

The present invention relates to dental materials for the control of caries and paradentitis. More specifically, the present invention relates to dental materials comprising antibacterial active agents and dental carrier materials for prophylactic and therapeutic control of caries and paradentitis, and in particular, dental neck caries.

Despite research over many decades and numerous attempts to achieve prophylactic and therapeutic treatment of caries and paradentitis, they remain an unmastered problem.

Medical treatment has hitherto been largely based on fluorides, c.f. Dr. Hans Joachim Schmidt, *Zahnhalskariesprophylaxe durch Fluoride,* Dr. Alfred Huthig Verlag, Heidelberg, 2d ed. 1967. It is only appropriate, however, to administer fluoride tablets up to the end of tooth formation, i.e., up to about 12 years of age. After this time, it is mainly a question of the local application of active substances for the prophylactic and therapeutic treatment of caries and paradentitis.

Fluorides and other active substances and in particular antimicrobial active substances have hitherto been largely incorporated into mouth and tooth treatment products and have been used during daily oral hygiene. The action period of these various treatment products is, however, relatively short in duration and provide only brief treatment since the active substances are rapidly diluted and rinsed out from salivation and absorption by food.

To obviate these disadvantages, it has been proposed that for the therapeutic treatment of paradentitis, antimicrobial active substances such as chlorhexidine embedded in a film as a system with delayed active substance delivery be introduced into the parodontium, c.f. Coventry, J. and Newman, H. N., *J. Clin. peridontol.,* 9, pp. 129-133 (1982) and Friedman, M. and Golomb, G., *J. Clin. Peridontol.,* 17, pp. 323-328 (1982). A further chlorhexidine-containing system with delayed active substance delivery for use in the dental area was described by T. E. Balanyk and H. J. Sandham in *J. Dent. Res.,* 64, pp. 1356-1360 (1985). It consists of a solution of a chlorhexidine salt in benzoin resin, which forms a firm film on drying from which the active substances is delivered in a delayed manner. The described in vitro test reveal that after 14 days only 3 to 10 mg. of chlorhexidine had been supplied by the system, and the remaining active substance was not available. Table 1 shows that the antiseptics thymol and iodine are the least effective.

OBJECTS OF THE INVENTION

Accordingly, it is the object of the present invention to provide an agent for the effective prophylactic and therapeutic control of caries and paradentitis.

It is further a particular object of the present invention to provide an agent for the effective prophylactic and therapeutic control of dental neck caries.

It is another object of the present invention to provide such an agent which remains over a long period or permanently in the oral cavity for prolonged action period as a treatment agent for the mouth and teeth while avoiding the disadvantages described above.

It is a further object of the present invention to provide such an agent having improved antimicrobial activity while also hardening the dentine which is subject to microbial attack.

BRIEF SUMMARY OF THE INVENTION

Increased microbicidal activity is obtained by using a combination of antimicrobial active agents thymol and/or carvacrol with chlorhexidine and/or physiologically compatible salts thereof in a dental material. The carrier for the active agent combination can be any dental material which can be hardened or is hard and form which the active substances can diffuse into the dentine.

DETAILED DESCRIPTION OF THE INVENTION

It has surprisingly been found that the inventive use of a combination of the antimicrobial active agents thymol and/or carvacrol of formulas

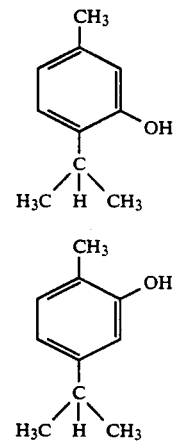

and the antimicrobial active agent chlorhexidine of formula

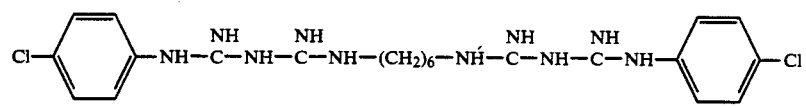

and/or physiologically compatible salts thereof in a dental material, results in an increase in the microbicidal activity of these substances. In addition, there is surprisingly a significant and selective hardening of the carious dentine through the use of the active substance combination of thymol and/or carvacrol and chlorhexidine or salts thereof in a dental material.

The active agent combination can be used in any dental material as a carrier, which can be hardened or is hard and from which the active substances can diffuse. Preferably, use is made of a material from which the active substances can diffuse into the dentine.

According to the invention, the term "dental material" covers those carrier materials which remain for a certain period of time, from hours to years in the oral cavity.

According to a preferred embodiment of the invention, the carrier comprises a solution of colophony in an organic solvent, preferred particular solvents being ethanol, propanol and amyl acetate. Good results have also been obtained using 1,2 dichloroethylene. The solution can be applied to the dental neck by painting, dripping or spraying and form there a firmly adhering varnish, which serves as the active agent reservoir and from which the active agent combination uniformly and completely diffuses into the dentine.

It has also proved effective to apply the dental material, e.g., as a dental varnish to a solid substrate, where it optionally may harden. According to the invention, the term "solid substrate" indicates substrates like artificial teeth, crowns and bridges, toothpicks, dental floss or toothsilk and devices of like nature, to which the dental material of the invention can be applied, and subsequent to the use or mounting thereof in the oral cavity, the combination of the invention can develop its activity.

As an example, a tooth varnish may be applied to the tip of a toothpick and the active agent combination of the invention may be applied to the teeth when cleaning the same.

According to further embodiments of the invention, the active agent combination is incorporated into dental materials such as cement, underfilling, filling, sealing, fixing, prosthetic, crown and bridge materials, as well as materials for producing prostheses or adhesives.

Thymol and carvacrol is used in a quantity of approximately from 10 to 0.05% by weight, preferably from 5 to 0.25% by weight, and in a particularly preferred manner from 2 to 0.5% by weight, in each case based on the dental material. Chlorhexidine is used in a quantity of approximately from 2 to 0.01% by weight, preferably from 1 to 0.05% by weight and in a particularly preferred manner, from 0.5 to 0.1% by weight, also based on the dental material. The aforementioned active substances can be used as such, or in the form of their physiologically compatible salts.

Usable chlorhexidine salts are, e.g., chlorhexidine-di-D-gluconate, chlorhexidine-dihydrochloride and chlorhexidinediacetate. According to the invention, it is also possible to use related compounds of chlorhexidine such as alexidine, picloxydine or vantocil, as well as those of thymol, such as, e.g., aristol.

The inventive dental material can also contain fluoride ions, e.g., in the form of sodium fluoride, in quantities of, e.g., from 5 to 0.05 and preferably from 2 to 0.1% by weight, based on the total formulation. In place of fluoride ions, it is also possible to use zinc ions, e.g., as chlorides or acetate; tin ions, e.g., as chloride; divalent copper ions, e.g., as copper nitrate and molybdenum ions, e.g., as $Na_2MoO_4 \cdot 2H_2O$ or mixtures thereof.

The inventive dental material acts both prophylactically and therapeutically against bacteria, the action time being essentially dependent on the carrier system chosen. If, for example, according to a preferred embodiment of the invention, a solution of colophony is used in high percent ethanol, then it can be painted, dripped or sprayed as a varnish, particularly onto the dental neck. This varnish adheres for a certain time, and during this period delivers the active substances contained in an almost complete form to the dental neck. Although the varnish is removed after a relatively short time by saliva, it maintains its therapeutic action over a longer period. Surprisingly, there is a rapid diffusion of the inventive active substance combination into the dentine and from there a uniform delivery of active agent takes place. This result was not foreseeable nor expected. The susceptibility of the dental neck to bacteria is consequently considerably reduced and, to the extent that an attack has already taken place, the dentine is hardened and stabilized against the spread of the attack.

Carrier materials for dental varnishes may also include shellac, benzoin resin, polyvinylpyrrolidone or other artificial or natural resins, which can be dissolved in a solvent and become hard after evaporation of the solvent.

If the inventive active agent combination is incorporated into cements or other dental materials, then a uniform active agent delivery can take place over a period of several weeks and months. For example, the inventive active agent combination can be incorporated into an underfilling material. Thereafter, the constant delivery of the active agents effectively prevents the occurrence of secondary caries.

It is also possible to incorporate the antibacterial substance combination into a light-hardening or conventionally curing filling material in order to decrease the rate of formation of secondary caries. Further, the active agents used according to the present invention can also be incorporated into prosthetic materials so that the finished prosthesis constantly delivers very small amounts of the active substances and consequently counteracts the spread of plaque, which would lead to caries on the natural teeth which are still present. The invention has a similar effect and result with false teeth.

Underfilling materials, filling materials, prosthetic materials, false teeth, etc. are well known to those of skill in the art and are outside the scope of the present invention. Such dental materials are, for example, disclosed in DE-OS 24 03 211, DE-OS 27 49 564 and U.S. Pat. No. 3,047,408.

The present invention is further illustrated by the following examples.

EXAMPLE I 3 g. of colophony is placed in a flask and mixed with 6 ml. of pure 96% ethanol, and thereafter, the flask is sealed and shaken for 24 hours until the colophony is completely dissolved. 2 ml. of distilled water is added to the solution, followed by 0.1 g. of thymol, 0.02 g. of chlorhexidine and 0.01 g. of sodium fluoride, and the mixture is again sealed and shaken until the agents are completely dissolved. The varnish obtained is stored in a sealed plastic vessel at room temperature.

EXAMPLE II

The activity of the varnish obtained according to EXAMPLE I on the dentine of healthy and carious cattle teeth was investigated according to the following procedure.

Cattle teeth were kept initially for 14 days at 37° C. in an artificial caries solution. The solution contained 6% by weight of carboxymethyl cellulose, and the pH value was 4.5. The teeth were completely covered with the solution throughout this period. The teeth were then removed, rinsed with water and dried.

In two successive tests, in each case 5 of the teeth being treated with the caries solution and 5 of the teeth being untreated, healthy cattle teeth were coated with the varnish prepared according to EXAMPLE I. The action of the varnish on the dentine hardness was determined by comparing the Knoop hardness (500 g. load) of the teeth treated, i.e., coated, with the varnish against teeth not treated with the varnish. The results are given in Table I.

TABLE I

| | Knoop Hardness Measurement Length of the Impression in μm | | | |
|---|---|---|---|---|
| | Dentine Without Caries | | Dentine With Caries | |
| TEST | Without Varnish | With Varnish | Without Varnish | With Varnish |
| 1 | 358 +/− 25 | 350 +/− 18 | 1233 +/− 9 | 970 +/− 71 |
| 2 | 356 +/− 24 | 343 +/− 29 | 1200 +/− 75 | 1063 +/− 61 |

The results show that hardness of the healthy, untreated dentine is not or is only insignificantly influenced by the inventive varnish prepared according to Example I. The hardness of the carious dentine, however, is significantly improved by the varnish treatment.

EXAMPLE III

The antimicrobial activity of the inventive active substance combination was proved in the agar diffusion test using streptococcus mutans.

The following test solutions were used:
A) Varnish according to Example I
B) Varnish according to Example I without fluoride ions
C) Varnish according to Example I without thymol
D) Varnish according to Example I without chlorhexidine 0.05 ml. of each solution was brought on to the streptococcus mutans-inoculated agar plates on a Petri dish and, the diameters of the inhibition zones were measure after incubation of the plates for 18 hours at 37° C. The results are given below in Table II.

TABLE II

| Test Solution | Inhibition Zone Diameter, (mm) |
|---|---|
| A | 20 |
| B | 20 |
| C | 15 |
| D | 13 |

The results given in Table II show that the antimicrobial effect of the combination of thymol and chlorhexidine is considerably improved compared with that of the individual components alone. The presence of fluoride ions, however, did not influence the inhibition zone diameter.

I claim:

1. A long-acting prophylactic and therapeutic dental material for the selective hardening of carious dentine and for the control of caries and paradentitis consisting essentially of a carrier and an antibacterial active substance diffusable into teeth from said carrier, said antibacterial active substance comprises a combination of a first component selected from the group consisting of thymol, carvacrol, and physiologically compatible salts thereof in an amount of from about 10 to about 0.05 weight percent of said dental material, and a second component selected from the group consisting of chlorhexidine and physiologically compatible salts thereof in an amount of from about 2 to about 0.01 weight percent of said dental material, said combination resulting in an improved antimicrobial effect adapted to be diffused into the tooth by diffusion from said carrier, said carrier comprising a member selected from the group consisting of dental cement, dental fillings, dental underfillings, dental sealing materials, crowns, bridges, prostheses and dental varnishes.

2. A method of selectively hardening carious dentine and controlling caries and paradentitis comprising:
A. forming a prophylactic and therapeutic dental material consisting essentially of an antibacterial active substance and a carrier, said antibacterial active substance consisting a combination of a first component selected from the group consisting of thymol, carvacrol, and physiologically compatible salts thereof in an amount of from about 10 to about 0.05 weight percent of said antibacterial active substance, and a second component selected from the group consisting of chlorhexidine and physiologically compatible salts thereof in an amount of from about 2 to about 0.01 weight percent of said antibacterial active substance, said combination resulting in an improve antimicrobial effect said carrier selected from the group consisting of dental cement, dental fillings, dental underfillings, dental sealing materials, dental fastening materials, crowns, bridges, prostheses, and dental varnishes;
B. applying said dental material to teeth;
C. continuously diffusing said antibacterial active substance into the dentine of said teeth from said carrier.

3. The dental material according to claim 1, wherein said first component is present in a quantity of from 5 to 0.25% by weight of said dental material, and said second component is present in a quantity of from 1 to 0.05% by weight of said dental material.

4. The dental material according to claim 1, wherein said first component is present in a quantity of from 2 to 0.5% by weight of said dental material, and said second component is present in a quantity of from 0.5 to 0.1% by weight of said dental material.

5. The dental material according to claim 1 further containing fluoride ions in an amount of from 5 to 0.05 weight percent of the total formulation.

6. The dental material according to claim 1, wherein said carrier is a dental varnish comprising a solution of colophony in an organic solvent.

7. The dental varnish according to claim 6, wherein said organic solvent is selected from the group consisting of ethanol, propanol and amyl acetate.

* * * * *